United States Patent [19]
Klammer

[11] Patent Number: 5,701,907
[45] Date of Patent: Dec. 30, 1997

[54] ELECTROCARDIOGRAPHIC WAVEFORM MONITORING METHOD AND SYSTEM

[75] Inventor: Peter J. Klammer, Salem, Oreg.

[73] Assignee: Hewlett-Packard Company, Palo Alto, Calif.

[21] Appl. No.: 766,072

[22] Filed: Dec. 16, 1996

[51] Int. Cl.⁶ .................................................. A61B 5/0402
[52] U.S. Cl. ........................................... 128/696; 128/901
[58] Field of Search ........................................ 128/702, 705, 128/706, 901, 703, 704, 696, 920

[56] References Cited

U.S. PATENT DOCUMENTS

| | | | |
|---|---|---|---|
| 3,825,015 | 7/1974 | Berkovits | 128/901 |
| 4,263,919 | 4/1981 | Levin | 128/901 |
| 5,010,887 | 4/1991 | Thornander | 128/901 |
| 5,417,221 | 5/1995 | Sickler | 128/696 |
| 5,598,848 | 2/1997 | Swanson et al. | 128/696 |

*Primary Examiner*—William E. Kamm
*Assistant Examiner*—Kennedy J. Schaetzle

[57] ABSTRACT

A method and system for use in an EKG system are provided for selecting from a number of different voltage threshold detectors that detector likely to yield the most reliable data to be utilized in determining whether the electrical activity of the heart is normal or abnormal. The method and system work by first specifying a particular window of time during which the outputs of the number of different voltage threshold detectors are to be observed. On the basis of the observation, different detectors are specified as either active or inactive. For those detectors specified as active, the times at which their thresholds were crossed during the specified window of time are recorded, and on the basis of these recorded times, the temporal regularity of threshold crossing for each detector is calculated. The detector with both the highest regularity of occurrence and the greatest magnitude threshold is then selected as the one likely to yield the most accurate data, unless other lower-in-magnitude detectors have the same regularity (within some user specified range of tolerance) as the one with the highest magnitude. In this case, if other lower-in-magnitude detectors have time rates of occurrence (a different measure than the temporal regularity) two times or more the time rate of occurrence of the highest magnitude-highest temporal regularity detector, then at least one of such lower-in-magnitude detectors can be chosen as being likely to yield the most accurate data.

20 Claims, 3 Drawing Sheets

ELECTROCARDIOGRAPHIC WAVEFORM MONITORING METHOD AND SYSTEM

BACKGROUND

1. Technical Field

The present invention relates, in general, to improved heart monitoring equipment to be utilized in monitoring EKG waveform data, and in particular, to improved heart monitoring equipment to be utilized in monitoring EKG waveform data having the ability to select from a number of different voltage threshold detectors that detector likely to yield the most reliable data to be utilized in determining whether the electrical activity of the heart is normal or abnormal. Still more particularly, the present invention relates to improved heart monitoring equipment to be utilized in monitoring EKG waveform data having the ability to select from a number of different voltage threshold detectors that detector likely to yield the most reliable data to be utilized in determining whether the electrical activity of the heart is normal or abnormal, with the selection being made on the basis of the temporal regularity and frequency of occurrence at which the thresholds of the individual detectors are met or exceeded.

2. Description of Related Art

The heart is generally described as being composed of four chambers: the right atrium, the right ventricle, the left atrium, and the left ventricle. There is a one-way valve between the right atrium and the right ventricle (the tricuspid valve). There is a one-way valve between the right ventricle and the arterial system which perfuses the lungs (the pulmonic valve). There is a one-way valve between the left atrium and the left ventricle (the mitral valve). And, lastly, there is a one-way valve between the left ventricle and the aorta (the aortic valve).

In terms of its functional operation, the heart receives oxygen-depleted blood via the vena cavae (the two large veins which return blood to the heart). These large veins empty into the right atrium. The right atrium then pushes this oxygen-depleted blood into the right ventricle. Next, the right ventricle pushes this oxygen-depleted blood into one long, continuous fluid path composed of, in sequence, the pulmonary artery, the capillary beds perfusing the lungs, and the pulmonary veins which empty into the left atrium. The continuous path ends with the left atrium, which is to say that there is no valve between the pulmonary veins and left atrium. Next, the oxygen-rich blood which has entered the left atrium is pushed into the left ventricle. Finally, the left ventricle pushes the blood out into the aorta.

The functional operation, described above, is effectuated by the electrochemical and mechanical operation of the heart as follows. The natural pacemaker of the heart, the sinoatrial nerve, discharges an electrochemical pulse, or action potential, and from this action potential all subsequent electrochemical and mechanical activity of the heart ensues. The sinoatrial nerve is located very near the right atrium, so the initial action potential reaches it almost immediately; simultaneously, the action potential propagates along a very fast conduction internodal tract to the left atrium, with the net result being that the atria (plural of atrium) receive the pulse almost simultaneously. Due to the anatomical structure of the heart, the atria initially receive the pulse upstream from the atrioventricular valves which separate the atria from the ventricles. When the pulse is received, the muscle fibers excited first contract first; in practice, what this means is that the atria of the region upstream contract first, so that the blood is pushed in the downstream direction. This operation is greatly analogous to the way in which toothpaste can be most efficiently squeezed out of the tube by squeezing at the closed end of the tube first.

Although, at this point, the atria have received the action potential, it (the action potential) is continuing to propagate throughout the heart. Simultaneous with the just-described actions involving the atria, the action potential is proceeding over three parallel internodal tracts to the atrioventricular node. The atrioventricular node functions as an analog delay; this delay provides time for atrial contraction to occur (the atria contract with more force over time as more fibers are recruited into contraction), which will enhance the functioning of the atria. After the delayed action potential leaves the atrioventricular nerve, it is conducted along a neural structure known as the bundle of His. Subsequent to this, the neural structure splits and the action potential is conducted by the right and left bundle branches to the regions of the right and left ventricles. Once the action potential arrives at the regions of the right and left ventricles, the action potential activates the Purkinje fibers, which are very fast conduction fibers that conduct the action potential very rapidly over and throughout the ventricles.

Once the ventricles are energized (depolarized), they begin to contract. The ventricles are much stronger and contract more rapidly than the atria (which are, at this point, continuing to contract). Very quickly, the pressure in the ventricular chambers outstrips that of the atria, causing both the mitral and the tricuspid valves to slam shut (because the pressure on the upstream side of these one-way valves exceeds the pressure on the downstream side). Once the right ventricle has outstripped the pressure of the contracting left atrium, the pulmonic valve opens and blood is pumped into the fluid path consisting of the pulmonic artery, capillary bed, pulmonary vein, and left atrium. Subsequent to this, once the left ventricle has outstripped the pressure of the aorta, the aortic valve opens and blood is pushed into the aorta. Once the ventricles have ejected the majority of their contents, the ventricles begin to relax and both the pulmonic and aortic valves close, with the pulmonic valve generally closing first due to the proximity of the continuing-to-contract left atrium.

Once the pressure in the relaxing ventricles falls below that of the continuing-to-contract atria, the atrioventricular valves (tricuspid and mitral) open and the atria push blood into the ventricles. Once the atria have completed this task, they relax and the heart enters a wait state after which the whole foregoing-described process is reinitiated by the next sinoatrial pulse.

As has just been discussed, the mechanical events of the heart are preceded and initiated by the electrochemical activity of the heart (i.e., the propagation of the action potential). There is also a device which transforms the electrochemical activity of the heart into a form visible to the human eye: the electrocardiograph, which produces a visual representation of the electrochemical activity of the heart. The visual representation is known as the electrocardiogram ("EKG"). Following is a brief description of the theory and operation of the electrocardiogram, after which the functioning of the invention as opposed to the prior art will be discussed.

The above description of the mechanical operation of the heart demonstrated that the mechanical events of the heart are controlled and sequenced by the propagation of an electrochemical pulse known as an action potential, but did not explain what the action potential is. A basic understanding of the action potential is essential to grasp the underlying theory of the EKG.

An action potential is a transient change in cell membrane potential which conveys information, such as the information in a signal telling a heart muscle fiber to contract. When the heart muscle is at rest, the electrical potential on either side of any cell membrane is maintained at a fixed potential. However, when the muscle is stimulated, either electrically, chemically, or mechanically, channels open in the membrane which allow the oppositely charged ions on either side of the membrane to cross the membrane, such ions engaging in an effort to reach electrical and thermal neutrality. This occurrence is referred to as "depolarization," since the system is becoming less polarized as the ions tend toward the lowest energy state. If the stimulation is great enough, the change in potential arising from the ions crossing the membrane will be great enough to depolarize the portion of the membrane directly adjacent to the area of the membrane depolarized by the stimulus. When this occurs, an action potential is said to have been initiated, and the signal will continue to propagate through the fiber via the just-described mechanism of depolarizing that portion of the membrane directly adjacent to the depolarized area. This propagation of the action potential is analogous to the way in which a row of dominoes falls when the first is flicked into the second, and the second falls into the third, and the third falls into the fourth, etc. Once the action potential has propagated past a region of the membrane, the cell membrane resets itself in a process known as "repolarization." In repolarization, ions are actively pumped back across the cell membrane to restore the polarized state.

In addition to the ions involved in the propagation of the action potential, there are numerous other free-floating ions distributed throughout the body. These ions will move under the influence of sufficiently strong electric fields. When the action potentials within the heart propagate, the ions moving across the cell membrane will disturb the electric fields within the body. This physiological electrochemical activity can be conducted to the body's surface via the reaction of the free-floating ions, which move in response to the electric-field effect of the charges crossing the membrane.

In the late 1800's, the Dutch physiologist Dr. Willem Einthoven developed techniques for recording this electrical activity of the heart, for which he was awarded a Nobel prize. The basic technique of Dr. Einthoven is still in use today. Dr. Einthoven's technique is known as the electrocardiogram, which is still referred to in honor of Dr. Einthoven as the EKG, which arises from the Dutch spelling of electrocardiogram.

During an EKG, electrodes are attached to the body surface. The electrodes are specially treated to allow the charge carrier within the electrodes (electrons) to communicate with the charge carriers within the body (ions) via electrochemical exchange. Attaching electrodes to the body surface allows the voltage changes within the body to be recorded after adequate amplification of the signal. A galvanometer within the EKG machine is used as a recording device. Galvanometers record potential differences between two electrodes. The EKG is merely the recording of differences in voltage between two electrodes on the body surface as a function of time, and is usually recorded on a strip chart. When the heart is at rest, diastole, the cardiac cells are polarized and no charge movement is taking place. Consequently, the galvanometers of the EKG do not record any deflection. However, when the heart begins to propagate an action potential, the galvanometer will deflect since an electrode underneath which depolarization has occurred will record a potential difference from a region on the body under which the heart has not yet depolarized.

A complete heart cycle is known as a heartbeat. On an EKG, the heartbeat has a distinctive signal. Initially, the galvanometer notes a relatively short duration rounded positive deflection (known as the P wave), which is believed to be caused by atrial depolarization. Subsequent to this, there is a small but sharp negative deflection (known as the Q wave). Next, there is a very large and sharp positive deflection (known as the R wave), after which there is a sharp and large negative deflection (known as the S wave). When these waves are taken together, they are known as the QRS complex. The QRS complex is believed to be caused by ventricular depolarization. Subsequent to the QRS complex is a relatively long duration rounded positive deflection (known as the T wave), which is believed to be caused by ventricular repolarization.

Over the years, health care professionals have built up a body of knowledge wherein they have learned to coordinate variations in and data from the EKG with different diseases and heart defects. Formally, this process of coordinating is known as "electrocardiography."

Within electrocardiography, EKG data serve many purposes. One of the purposes served is determining whether the heart is beating normally or abnormally; that is, whether or not the heart is following a normal predictable rhythm, or has instead fallen into a non-rhythmic condition indicative of the need for treatment. The rhythmicity of the heart is generally assessed via the use of voltage threshold detectors. These are detectors that indicate whether their voltage thresholds have been crossed. They are used to monitor the EKG waveform (or filtered versions of the EKG waveform, with such filtering being done to enhance the QRS complex) and whether its amplitude meets or exceeds certain threshold voltages. The rate at which the thresholds are exceeded is used to determine the rhythmicity of the heart. In addition, the same detectors can be used to determine the heart rate once it has been established that the heart is beating normally.

Determining whether or not the heart has entered a non-rhythmic state on the basis of EKG data is difficult. The difficulty arises from the fact that a strong healthy normally beating heart may manifest on an EKG as a waveform with a high amplitude, while a weaker or sicker normally beating heart may manifest on an EKG as a waveform of lesser amplitude. Furthermore, there are certain conditions, such as fibrillation, in which the heart activity manifests itself on an EKG as a waveform with no QRS complex and very low amplitude components.

The differing amplitudes of the various EKG waveforms of the heart make the determination of the rhythmicity difficult in that if the heart is beating normally, generally the best heart rate detection algorithm to use is one where the magnitude threshold on the detector monitoring the EKG is set high, so that the algorithm will only detect the QRS complex (which, as discussed above, is indicative of ventricular contraction) and not be fooled by the low-magnitude P, T, or U complexes; conversely, if the heart has entered fibrillation, the best detection algorithm to use is one where the magnitude threshold on the detector is set low, because fibrillation usually manifests on an EKG as waveform with very low amplitude components. Thus, in light of the fact that the heart activity can manifest itself as many very different amplitude waveforms, the problem arises as to how to choose the best voltage threshold detector under the circumstances to monitor and determine the rhythmicity and rate of the heart.

The need for a device to adequately assess the rhythmicity of the heart is crucial for many conditions, but in particular in determining whether to apply a defibrillation pulse to the heart. "Fibrillation" is a term coined in the mid-to-late 1800's and refers to a condition in which the above described synchronous movement of the action potential through the heart becomes unsynchronized to the point such that it appears each muscle fiber of the heart is contracting randomly and independent of the other fibers; that is, to the point where action potentials are spontaneously arising throughout various regions of the heart at random and unsynchronized times. Since the muscle fibers where the spontaneous action potentials occur contract, and since this contraction is not in any way synchronized with the other action potentials, the result is chaotic, with the net effect being that no blood is pumped out of the heart because the different parts of the heart muscle are not acting in synchrony. In fact, a heart in fibrillation is often described as resembling a quivering bag filled with worms, since the asynchronous contractions of different bands or fibers of muscle resembles the surface of a bag filled with writhing worms.

"Defibrillation" is the causing of the cessation of the chaotic and uncoordinated contraction of the ventricular myocardium arising from the spontaneously occurring action potentials by the application of an electrical voltage and current pulse. Defibrillation is achieved when the electrical energy supplied is large enough to depolarize a major portion of the heart muscle such that virtually the entire heart muscle is simultaneously depolarized. Once this is done, all portions of the heart muscle repolarize virtually simultaneously and the heart is in its resting state. An analogous way to think of defibrillation is the resetting of the heart to its wait state. Then, once the sinoatrial nerve fires, the heart muscle propagates the action potential in the correct synchronous fashion, since the defibrillation puts all portions of the heart back in synch.

The criteria as to whether a defibrillation pulse will be applied is the rhythmicity of the heart. If a heart is in or appears to be entering a non-rhythmic state, a defibrillation pulse is often supplied.

A grave concern when using defibrillators is the ensurance that the heart is actually in fibrillation before a pulse is applied, because applying a defibrillation pulse to a heart not in fibrillation will often induce fibrillation. Thus, it is apparent that a need exists for a device which will give adequate assessment of the rhythmicity and rate of the heart even for waveforms of varying amplitudes and waveforms without QRS complexes, e.g. fibrillation waveforms.

The prior art has not addressed the problems arising from the fact that various heart conditions manifest as EKG waveforms with different amplitudes. In the prior art, a number of different voltage threshold detectors are utilized. The data from each of these detectors are constantly being monitored during certain specified windows of time. Generally, the highest threshold monitor which registers a threshold crossing during the specified window of time is used to determine the rhythmicity and rate of the heart. That is, the prior art method merely selects one from a number of possible voltage threshold detectors solely on the basis of whether the threshold of the detector was exceeded during a specified window of time.

Since the prior art solution makes no attempt to select the appropriate detector for use on the basis of the qualitative nature of the waveform detected, but rather only uses the largest magnitude detector whose threshold has been exceeded, there is a danger that the prior art method will register a lack of rhythmicity in a heart beating normally but with low amplitude (such as when the decreased amplitude waveform occasionally spiked into the high magnitude detector region). The prior art never addresses the problem of what to do when one is in the "gray area" of a normally beating heart but with low or varying amplitude, and how to make a qualitative assessment of the rhythmicity of the heart under such conditions.

In view of the foregoing, it is apparent that a need exists for the present invention: a method and system which can select from a number of different voltage threshold detectors that detector likely to give the most accurate data with respect to whether the heart is beating normally or abnormally, as indicated by EKG waveforms of widely varying amplitudes.

SUMMARY OF THE INVENTION

It is therefore one object of the present invention to provide improved heart monitoring equipment to be utilized in monitoring EKG waveform data of widely varying amplitudes.

It is another object of the present invention to provide improved heart monitoring equipment to be utilized in monitoring EKG waveform data of widely varying amplitudes and having the ability to select from a number of different voltage threshold detectors that detector likely to yield the most reliable data to be utilized in determining whether the electrical activity of the heart is normal or abnormal.

It is yet another object of the present invention to provide improved heart monitoring equipment to be utilized in monitoring EKG waveform data of widely varying amplitudes and having the ability to select from a number of different voltage threshold detectors that detector likely to yield the most reliable data to be utilized in determining whether the electrical activity of the heart is normal or abnormal, with the selection being made on the basis of the regularity and frequency of occurrence at which the thresholds of the individual detectors are met or exceeded.

The foregoing objects are achieved as is now described. A method and system for use in an EKG system are provided for selecting from a number of different voltage threshold detectors that detector likely to yield the most reliable data to be utilized in determining whether the electrical activity of the heart is normal or abnormal. The method and system work by first specifying a particular window of time during which the outputs of the number of different voltage threshold detectors are to be observed. On the basis of the observation, different detectors are specified as either active or inactive. For those detectors specified as active, the times at which their thresholds were crossed during the specified window of time are recorded, and on the basis of these recorded times, the temporal regularity (i.e., an assessment as to how the times at which the threshold was exceeded are distributed about a mean time interval of occurrence; that is, an assessment as to how predictable that time was at which a particular detector's threshold was crossed) of threshold crossing for each detector is calculated. The detector with both the highest regularity of occurrence and the greatest magnitude threshold is then selected as the one likely to yield the most accurate data, unless other lower-in-magnitude detectors have the same regularity (that is, within some user specified range of tolerance) as the one with the highest magnitude. In this case, if other lower-in-magnitude detectors have time rates of occurrence (which is a different measure than the temporal regularity) two times or more the time rate of occurrence of the highest magnitude-highest temporal regularity detector, then at least one of such lower-in-magnitude detectors can be chosen as being likely to yield the most accurate data.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF PREFERRED EMBODIMENT

Figure 1:
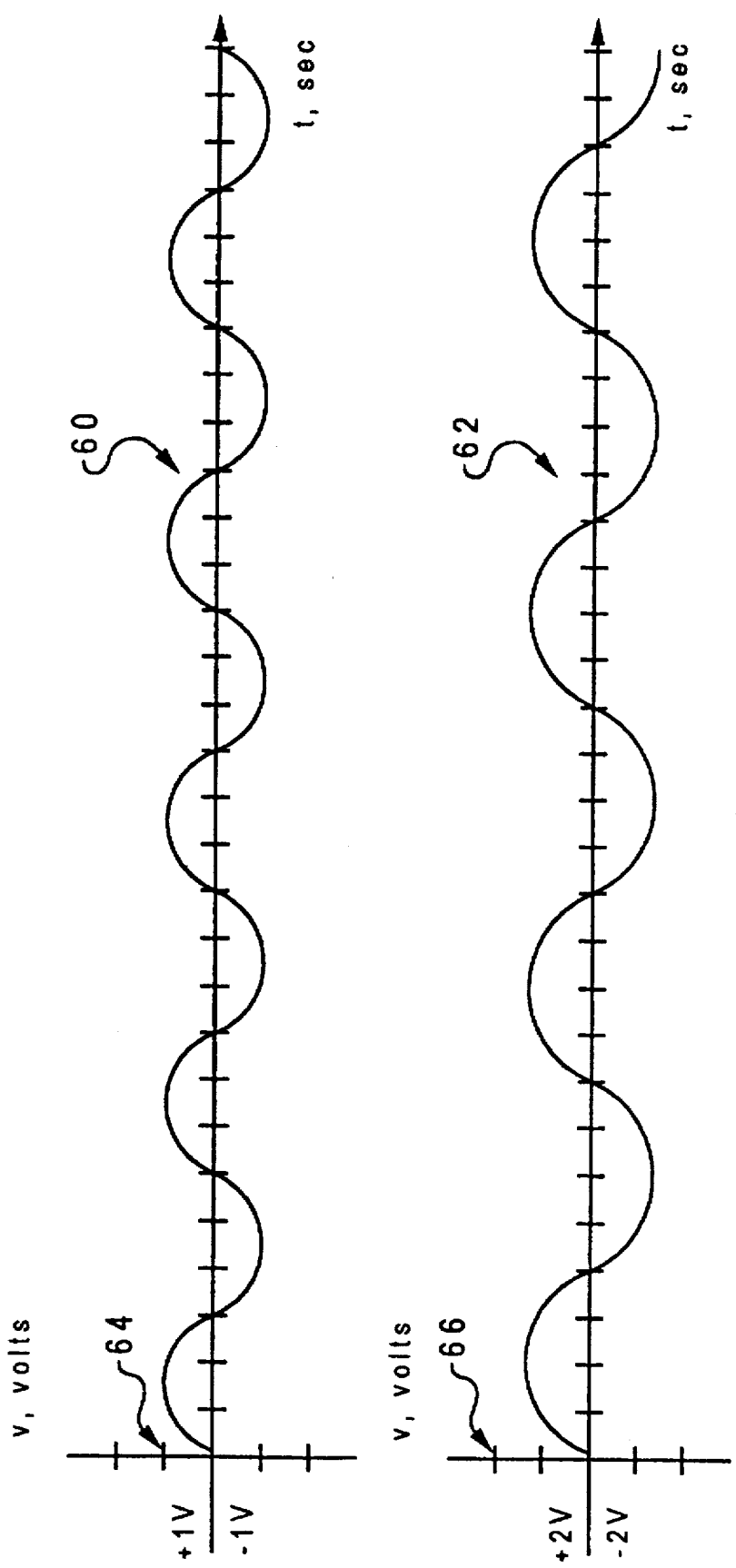
FIG. 1 depicts two different waveforms, along with two different voltage thresholds, and is used to illustrate the overall concept of temporal regularity.

The present invention provides a method and system for selecting from a number of different voltage threshold detectors that detector likely to yield the most reliable data to be utilized in determining whether the electrical activity of the heart is normal or abnormal. The method and system are to be used in conjunction with EKG monitoring devices, which produce EKG waveforms which are fed into the different voltage threshold detectors. The method and system work by first specifying a particular window of time during which the outputs of the threshold detectors are to be observed. On the basis of the observation, different detectors are specified as either active or inactive. And for those detectors specified as active, the times at which their thresholds were met or exceeded during the specified window of time are recorded.

On the basis of these recorded times, the temporal regularity (i.e., an assessment as to how the times at which the threshold was exceeded are distributed about a mean time interval of occurrence; that is, an assessment as to how predictable that time was at which a particular detector's threshold was crossed) of threshold crossing for each detector is calculated. Next, the detector with both the highest regularity of occurrence and the greatest magnitude threshold is selected as the one likely to yield the most accurate data, unless other lower-in-magnitude detectors have the same regularity (that is, within some user specified range of tolerance) as the one with the highest magnitude. In this case, if the lower-in-magnitude detectors have time rates of occurrence (which is a different measure than the temporal regularity) two times or more the time rate of occurrence of the highest magnitude-highest temporal regularity detector, then at least one of such lower-in-magnitude detectors can be chosen as being likely to yield the most accurate data; otherwise, the highest magnitude-highest regularity detector is chosen.

As stated, the present invention uses both (1) the temporal regularity of the signal crossing the threshold of a particular detector and (2) the time rate of occurrence of the signal crossing the threshold of a particular detector. Both of these measures explicitly involve the time of threshold crossing.

The time rate of occurrence of the signal crossing the threshold of a particular detector is relatively easy to understand, and can be thought of as the total number of instances of the signal crossing the threshold during some specified window of time divided by the duration of the specified time window.

The temporal regularity is somewhat more difficult to understand. The temporal regularity is based upon statistical concepts and refers to the "spread" of data about some measure of central tendency (e.g., the mean or median of the time interval of occurrence of the data) regarding the time interval between occurrences of threshold crossing. It is tempting to think of the temporal regularity as being analogous to periodicity, but such should not be done. The reason this should not be done is that two different waveforms could have very different time periods and yet the same or similar measures of temporal regularity. This is because temporal regularity is built upon the concept of variation around a central tendency of the interval of occurrence.

After the times of threshold crossing for particular voltage threshold detectors have been collected, the measure of central tendency for the different detectors can be calculated for a particular detector. The analysis begins with the calculation of a single number, which will summarize or represent all the data for a specific detector. Because collected data often exhibit a cluster or central point, this number is called a measure of central tendency. The most frequently utilized measure is the simple arithmetic average, which is the sum of all the time intervals between threshold crossings divided by the total number of threshold crossings during the specified window of time; because there are many more measures of central tendency which can be logically thought of as the average, this simple arithmetic average is referred to by a special name, "the mean."

In addition to the mean, the median is another frequently used measure of central tendency. The median is more of a counting concept than an averaging concept, which may be confusing since both it and the mean are often lumped together under the rubric of "measures of central tendency"; that is, to get the median you don't average the values of the data collected at all—instead you deal with the total count of the number of intervals recorded. To understand the concept of the median imagine that the recorded time intervals could all be arranged along a number line, from the smallest value of the recorded interval to the greatest value of the recorded interval. If the total number of time intervals recorded was odd (e.g., if you recorded three intervals, one of duration 3 seconds, one of duration 6 seconds, and another of duration 2 seconds), then the median would be the point about which the total number of points were the same on either side of that point (e.g. the interval of duration 3 seconds in the preceding example). On the other hand, if the total number of time intervals recorded was even (e.g., if you recorded four intervals, one of duration 3 seconds, one of duration 6 seconds, one of duration 20 seconds, and another of duration 2 seconds), one can see that there would not be any clear middle value if the four samples were laid out on a number line, so what is done is to take the arithmetic average of the two middle values (e.g. to add 3 seconds plus 6 seconds, and divide by two) and call the result the middle value, and treat it as a sort of "central point" about which there are equal number of points (e.g., there is one point on either side of the "central point" formed by the average of the two middlemost values).

As discussed, the concept of temporal regularity involves measures of variation about the measure of central tendency. The variability of the distribution refers to whether the measurements are clustered tightly around the mean or spread widely about it. One measure of this variability could be the difference between two percentiles, say the 25th and the 75th percentiles. In this measure, first the allowable range of values of time intervals is specified. Next, the recorded time intervals are examined relative to each allowable value and the total percentage of recorded time periods below that value are calculated. The term percentile means that the percent of the measurements are less than or equal to it; in particular, the 25th and the 75th percentiles are called the lower and upper quartiles, respectively.

A more commonly used measure of deviation is the standard deviation. The standard deviation is a measure of variability that has been rather arbitrarily defined to be, for data with the mean x, the square root of the mean of the squares of the deviations; it is usually designated by the Greek letter sigma ($\sigma$). The square, $\sigma^2$, of the standard deviation is called the variance. If the standard deviation is small, the measurements are tightly clustered around the mean; if it is large, they are widely scattered. The standard deviation is a measure which gives a good feel for how scattered the data are, and is hence a good measure of variation from the central tendency. There are many other measures of variation about the central tendency, such as variance, range, trimmed range, mean absolute deviation, et cetera.

Thus, the term and concept of temporal regularity, as used in this specification, incorporates both the concepts of central tendency and variation about the central tendency. Specifically, it can now be seen that the temporal regularity refers to how statistically likely it is that the threshold of a detector will be crossed after or before a particular central tendency for the interval of time measured.

Although the preferred embodiment of the invention, discussed below, will only address the use of one subset of the measures of central tendency and variations from same, one skilled in the art will recognize that any measure of central tendency and variation from same can be used to good effect in the disclosed invention.

As noted above, the temporal regularity for two waveforms of vastly different times of occurrences can be identical. Because abstractions are difficult to deal with in the absence of specifics, the following example is given.

With reference now to the figures, and in particular with reference now to FIG. 1, there are depicted two sinusoidal waveforms. These waveforms are presented to illustrate the difference between temporal regularity and time rate of occurrence, but the idea will be the same for EKG waveforms which have quite a different morphology than sine waves. FIG. 1 illustrates a first sine wave 60 with a period of 6 seconds. FIG. 1 also shows a second sine wave 62 with a period of 8 seconds. Also depicted is a voltage threshold 64 of one volt has been chosen for the first sine wave 60. Also illustrated is a voltage threshold 66 of two volts has been chosen for the second sine wave 62.

Arbitrarily choosing a window of time of 30 seconds, it can now be illustrated that these sine waves with different periods will yield different rates of occurrences and yet both waves will have the same temporal regularity. The first sine wave 60 crossed the 1 volt threshold at 1.5, 7.5, 13.5, 19.5, and 25.5 seconds within the 30 second window. The second sine wave 62 crossed the 2 volt threshold at 2, and 10, 18, and 26 seconds. The time rate of occurrence for the first sine wave 60 is 5 crossings/30 seconds, or 0.17 crossing/second. The time rate of occurrence for the second sine wave 62 is 4 crossing/30 seconds, or 0.13 crossings/second. These two time rates of occurrence are radically different.

To calculate the temporal regularity, for sake of illustration the mean is used as the measure of central tendency. The equation for the mean is the sum of value of the intervals of occurrence divided by the number of samples (number of intervals recorded), n, expressed in symbols as:

$$\bar{x} = \frac{\Sigma x}{n}$$

The first sine wave 60 crossed the 1 volt threshold 64 at 1.5, 7.5, 13.5, 19.5, and 25.5 seconds within the 30 second window; this yields the following time intervals 6 seconds (7.5−1.5), 6 seconds (13.5−7.5), 6 seconds (19.5−13.5), and 6 seconds (25.5−19.5). The second sine wave 62 crossed the 2 volt threshold 66 at 2, and 10, 18, and 26 seconds; this yields the following time intervals 8 seconds (10−2), 8 seconds (18−10), and 8 seconds (26−18). Using the equation for the mean with the measurements taken from the first sine wave 60, it can be seen that the mean time interval of occurrence of threshold crossing is 6 seconds (the sum of the time intervals between recorded times of threshold crossing divided by 4, the total number of intervals). Using the equation for the mean with the measurements taken from the second sine wave 62, it can be seen that the mean is 8 seconds (the sum of the time intervals between recorded times of threshold crossing divided by 3, the total number of intervals). The standard deviation of the measurements taken from the first sine wave 60 is zero, using the formula for standard deviation given above; likewise, the standard deviation of the measurements taken from the second sine wave 62 is zero.

From the standpoint of this specification, the two waveforms 60, 62 have identical measures of temporal regularity, even though the two waveforms 60, 62 have vastly different periods and time rates of occurrence of threshold crossing. Thus, one advantage of the present invention can be seen: it will allow the proper selection of a voltage threshold detector based upon the assessment of the relative rhythmicity with which the threshold of different voltage threshold detectors are crossed, an assessment that may not at all be apparent upon visual or time rate of occurrence inspection.

Figure 2:
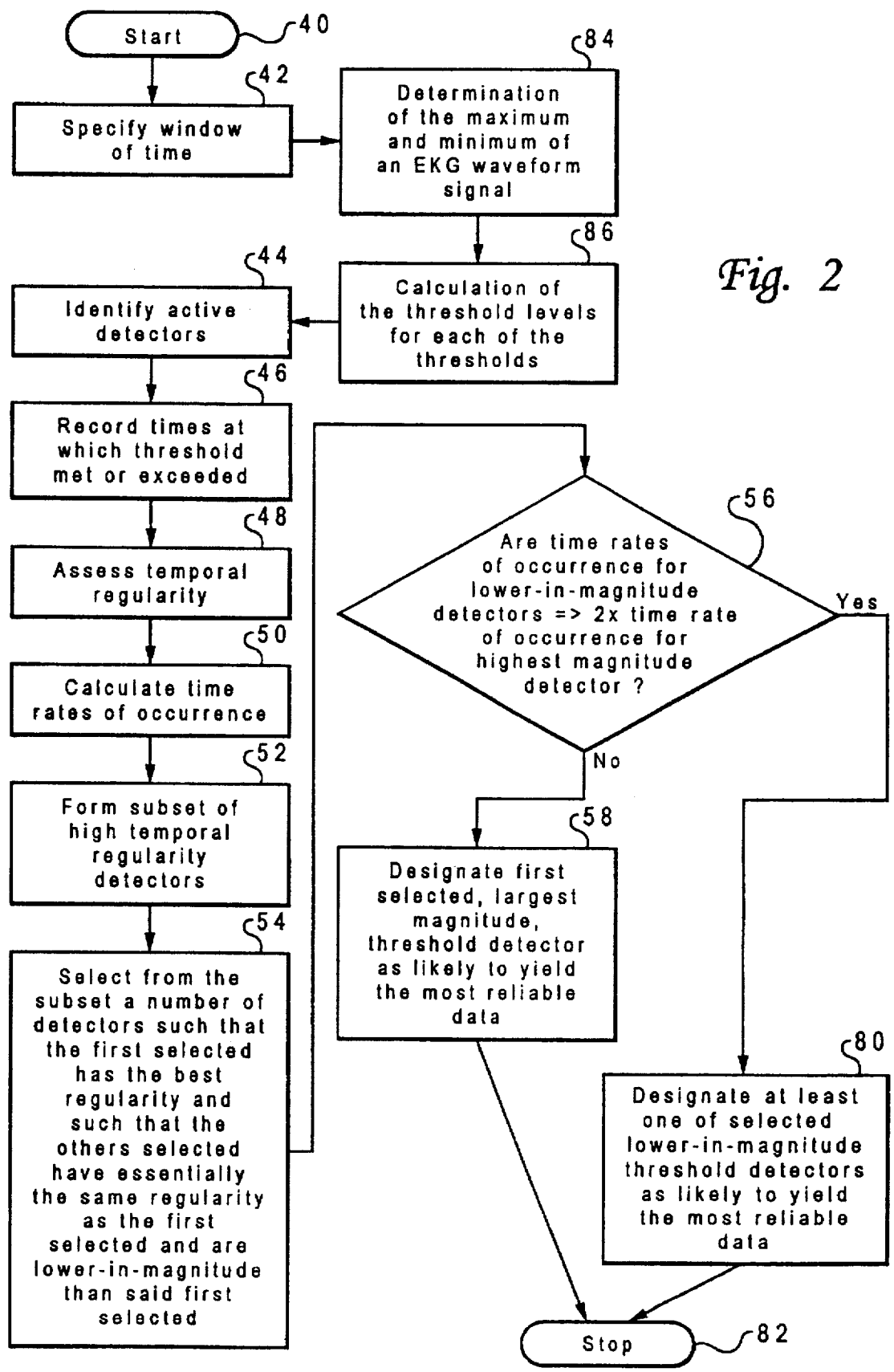
FIG. 2 is a high-level logic flowchart of an illustrative embodiment of the method of the present invention.

Referring now to FIG. 2, which is a high-level logic flowchart of an illustrative embodiment of the method of the present invention.

Step 40 shows the beginning the process. Step 42 depicts the method step wherein the duration of a window of time is specified. Step 84 illustrates the determination of the maximum and minimum of an EKG waveform signal occurring during the window of time specified in step 42. Step 86 shows the calculation of the voltage threshold levels for each of the "voltage threshold detectors"; that is, the calculated voltage threshold levels are treated in the invention as if they actually were "voltage threshold detectors". These calculated thresholds are a fixed percentage of the maximum and minimum signal levels determined in step 84, and in the preferred embodiment equate to ninety (90), seventy (70), fifty (50), thirty (30), and ten (10) percent of the maximum and minimum threshold level. There are also fixed positive and negative threshold levels (called floor thresholds) which can serve as the absolute minimum threshold level that can be used for any waveform. If the amplitude of the EKG waveform signal as determined by step 84 is lower than some preset level, then the foregoing floor values are decreased appropriately; for example, the floor thresholds could be adjusted by dividing them by two, three, four, etc.

Next, method step 44 illustrates the identification of the number of voltage threshold detectors 14 deemed active during the window of time specified in method step 42. A voltage threshold detector 14 is deemed to be active (1) if its voltage threshold is greater than a predetermined minimum voltage (with such predetermined minimum voltage threshold being the floor threshold discussed previously); (2) if it had greater than a predetermined minimum number of threshold crossings (e.g., three) within the window of time specified in step 42; and (3) if its threshold crossings spanned a large predetermined percentage (e.g., fifty percent) of the window of time specified in step 42. As a short hand notation, the exceeding of the voltage threshold of a specific voltage threshold detector 14 will be referred to as the "crossing" of the voltage threshold detector 14. Furthermore, all different verb forms of the verb "cross" will also encompass within them the concept of exceeding the threshold value for any particular voltage threshold detector 14.

Method step 46 shows the recording of times at which the voltage threshold was met or exceeded for each individual voltage threshold detector 14 deemed to be active in method step 44. That is, for each individual voltage threshold detector 14 deemed to be active, there are recorded the times at which the thresholds of those active voltage threshold detectors 14 are crossed.

Method step 48 illustrates the assessment of the temporal regularity as to how often the thresholds of the active voltage threshold detectors 14 were crossed. To adequately assess the temporal regularity of the crossing of the thresholds of the active voltage threshold detectors 14, an operation such as that discussed in reference to FIG. 1, or analogous to it is engaged in. In order to assess the temporal regularity of a specific voltage threshold detector 14, first the time intervals between threshold crossing for that particular are calculated based upon the recorded times discussed in method step 46. Once the interval between threshold crossings for that specific voltage threshold detector 14 have been calculated, the measure of central tendency for the intervals of occurrence is calculated. Next, the variation of the calculated intervals of distribution about that measure of central tendency are calculated. The resulting number then serves as a measure of temporal regularity. This process of accessing temporal regularity is engaged in for every voltage threshold detector 14 deemed to be active in method step 44.

Method step 50 depicts the calculating of the time rates of occurrence of threshold crossing. This method step is engaged in for all voltage threshold detectors 14 deemed to be active in method step 44. In order to calculate the time rate of occurrence, for any specific active voltage threshold detector 14, one could divide the total number of threshold crossings by the time duration of the window of time specified in method step 42. In the current implementation, a trimmed mean of the intervals is calculated and then the rate is calculated from this. The trimmed mean is calculated by ordering a set of numbers from smallest to largest, trimming off a certain percentage of the numbers at either end of the distribution, and then calculating the mean using the remaining, untrimmed, numbers. However, in the preferred embodiment the time rate of occurrence can be calculated using any measure of central tendency (e.g. mean, median, trimmed mean, etc.) of the intervals between threshold crossings.

Thus, the rate in beats per minute can be calculated as follows:

$$bpm = 60 * \frac{1}{x}$$

And where such measure of central tendency could be, for example, the mean, the median, the trimmed mean, etc.

Method step 52 illustrates the formation of a subset of high temporal regularity voltage threshold detectors 14 from the set of voltage threshold detectors 14 deemed to be active in method step 44. That is, within this method step, only those voltage threshold detectors 14 deemed to be active in method step 44 which are assessed as having high temporal regularity are retained within the subset.

Method step 54 depicts the selection of a number of active voltage threshold detectors 14 from the subset formed in method step 52. The voltage threshold detectors 14 selected are that voltage threshold detector 14 with the highest assessed temporal regularity along with those lower-in-magnitude voltage threshold detectors 14 with assessed temporal regularity essentially equivalent (that is, within some user specified range of tolerance) to that of the voltage threshold detector 14 with the highest assessed temporal regularity.

Method step 56 shows a decision point. In this decision point, the time rates of occurrence of the lower-in-magnitude voltage threshold detectors 14 selected in method step 54 are compared with the time rate of occurrence of the highest assessed temporal regularity voltage threshold detector 14 selected in method step 54. If the time rates of occurrence of the lower-in-magnitude voltage threshold detectors 14 selected in method step 54 are found to be two times or more that of the time rate of occurrence of the highest assessed temporal regularity voltage threshold detector 14, then at least one of such lower-in-magnitude voltage threshold detectors 14 selected in method step 54 are designated as being likely to yield the most accurate data to be utilized in determining whether or not the electrical activity of the heart is normal or abnormal as is shown in method step 80. Further depicted in method step 58 is that if the time rates of occurrence of the lower-in-magnitude voltage threshold detectors 14 selected in method step 54 are not two times or more of that of the highest assessed temporal regularity voltage threshold detector 14 selected in method step 54, then the highest assessed temporal regularity voltage threshold detector 14 selected in method step 54 will be designated as that voltage threshold detector 14 likely to yield the most accurate data to be utilized in determining whether the electrical activity of the heart is normal or abnormal. Method step 82 shows the stopping or the end of the process.

Figure 3:
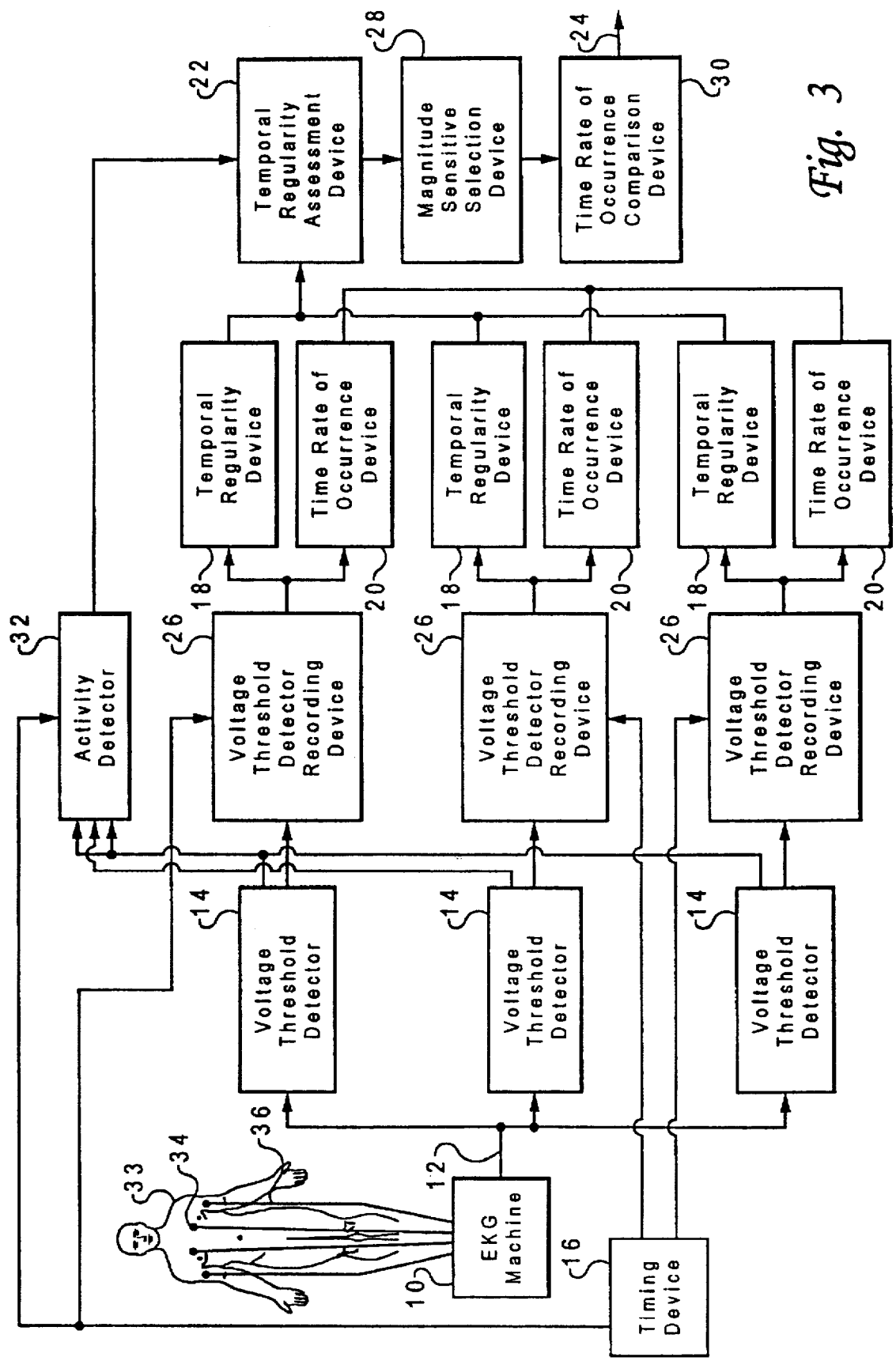
FIG. 3 illustrates a high-level schematic view of a system for implementing the present invention.

With reference now to FIG. 3 there is illustrated a high level schematic view of a system for implementing the present invention. In the preferred embodiment, the system shown in FIG. 3 is a Codemaster 100 defibrillator with the Shock Advisory Option, manufactured by the Hewlett-Packard Company. Alternately, the system shown in FIG. 3 could also be a Codemaster XL or XL+ defibrillator with the Shock Advisory Option, also manufactured by the Hewlett-Packard Company. Another alternate embodiment has been contemplated where the system shown in FIG. 3 is a cardiograph, Holter monitor, or other medical device.

The components of the invention are shown for clarity of understanding as discrete blocks, but it should be understood that each discrete block can be implemented as either hardware or software or a mixture of the two. For example, the voltage threshold detectors 14 are shown for clarity of understanding as discrete blocks, but in the preferred embodiment they can merely be calculated voltage levels, deemed to be equivalent to such discrete voltage threshold detectors 14, as is done in method step 66. Likewise: the voltage threshold detector recording devices 26 are shown for clarity of understanding as discrete blocks, but in the preferred embodiment they can be implemented by keeping track of when the calculated voltage levels—deemed to be equivalent to voltage threshold detectors 14 are exceeded, as is done in method step 66. The same can be said for the remaining components illustrated in FIG. 3.

Depicted in FIG. 3 is a body 33 to which a number of electrocardiographic electrodes 34 have been attached. The electrocardiographic electrodes are illustrated as connecting to an EKG machine 10 via conducting wires 36. The EKG machine 10 produces a EKG waveform representation 12 of a heart. This EKG waveform 12 is fed to a number of different voltage threshold detectors 14, each of which has a different voltage threshold. The voltage threshold detector recording devices 26 record the times at which the voltage thresholds for their associated voltage threshold detectors 14 are crossed (that is, met or exceeded). The voltage threshold detector recording devices 26 record these times during a certain specified window of time. A timing device 16 supplies the voltage threshold detector recording devices 26 with the appropriate information as to when the window of time is to open and when the window of time is to close. Upon the closing of a specified of window time, the voltage threshold detector recording devices 26 output the recorded times at which their respective voltage thresholds were crossed. Each voltage threshold detector recording device 26 outputs its recorded times to both a temporal regularity device 18 and a time rate of occurrence device 20.

The temporal regularity device 18 first calculates the intervals between each successive threshold crossing for the voltage threshold detector 14 associated with the voltage threshold detector recording device 26 from which the temporal regularity device 18 received the information. Once the temporal regularity device 18 has calculated the intervals between crossings, it then assesses a measure of central tendency of the calculated intervals of occurrence. Subsequent to this, the temporal regularity device 18 calculates the variation or spread of the calculated intervals about the measure of central tendency.

Contemporaneous with the activities of the temporal regularity device 18, the time rate of occurrence device 20 is calculating the time rate of occurrence of threshold crossings for that voltage threshold detector 14 associated with the voltage threshold detector recording device 26 from which it received its information. The time rate of occurrence is calculated in the same way as described in method step 50 of FIG. 2. As can be seen from FIG. 3, each individual voltage threshold detector recording device 26 has associated with it a temporal regularity device 18 and a time rate of occurrence device 20. What this means is that the temporal regularity and time rate of occurrence is assessed for each individual voltage threshold detector.

Once the temporal regularities and time rates of occurrence have been calculated for each voltage threshold detector that information is fed into the temporal regularity assessment device 22. The temporal regularity assessment device 22 only accepts as valid data corresponding to those voltage threshold detectors 14 designated as active by activity detector 32. The activity detector 32 designates as active those voltage threshold detectors 14 (1) with voltage thresholds greater than a predetermined minimum voltage threshold (with such predetermined minimum voltage threshold being the floor threshold discussed previously); (2) with greater than a predetermined minimum number of threshold crossings (e.g., three) within the window of time specified by timing device 16; and (3) with voltage threshold crossings spanning a large predetermined percentage (e.g., fifty percent) of the window of time specified by timing device 16. The temporal regularity assessment device 22 compares the temporal regularity of every device upon which it has received temporal regularity data (i.e., those voltage threshold detectors 14 designated as active during the window of time by activity detector 32) from the various temporal regularity devices 18 and determines which voltage threshold detectors 14 show a relatively high measure of regularity, as compared to a predetermined threshold number and forms a subset composed of those highly regular devices.

Once this has been done, the magnitude sensitive selection device 28 then selects from those remaining voltage threshold detectors 14 previously examined by the temporal regularity assessment device 22 that voltage threshold detector with the highest assessed temporal regularity, along with those lower-in-magnitude voltage threshold detectors 14 with assessed temporal regularity essentially equivalent (that is, within some user specified range of tolerance) to that of the voltage threshold detector with the highest assessed temporal regularity.

Next, the time rate of occurrence comparison device 30 compares the time rates of occurrence for the voltage threshold detectors 14 selected by the magnitude sensitive selection device 28. If the time rate of occurrence comparison device 30 determines that the time rates of occurrence of the lower-in-magnitude voltage threshold detectors 14 are two times or more that of the rate of occurrence of the highest assessed temporal regularity voltage threshold detector 14, then such lower-in-magnitude voltage threshold detectors 14 are designated as being those voltage threshold detectors 14 likely to yield the most reliable data to be utilized to determine whether the electrical activity of a heart is normal or abnormal, and information to that effect is output on output line 24. However, if the time rates of occurrence of the lower-in-magnitude voltage threshold detectors 14 are not two times or more of that of the highest assessed temporal regularity voltage threshold detector 14, then the highest assessed temporal regularity voltage threshold detector 14 is designated as that voltage threshold detector 14 likely to yield the most reliable data to be utilized to determine whether the electrical activity of a heart is normal or abnormal.

While an illustrative embodiment has been particularly shown and described, it will be understood by those skilled in the art that various changes in form and detail may be made therein without departing from the spirit and scope of the illustrative embodiment.

What is claimed is:

1. A method for selecting from a plurality of different voltage threshold detectors that detector likely to yield the most reliable data to be utilized in determining whether the electrical activity of a heart is normal or abnormal, said method to be utilized with EKG monitoring devices, and said method comprising the steps of:

specifying a particular window of time;

identifying certain voltage threshold detectors as active during said specified window of time;

recording the times at which a threshold of each of said active voltage threshold detectors was exceeded during said specified window of time;

in response to said recorded times, assessing the temporal regularity of how often said threshold of each of said active voltage threshold detectors was exceeded; and in response to said assessed temporal regularity, designating at least one of said active voltage threshold detectors as likely to yield the most reliable data to be utilized in determining whether the electrical activity of the heart is normal or abnormal.

2. The method of claim 1 wherein said recorded times have associated threshold crossing intervals, and said step of assessing the temporal regularity of how often said voltage thresholds of each of said active voltage threshold detectors was met or exceeded further comprises the step of computing the spread of the threshold crossing interval distribution.

3. The method of claim 2, wherein said step of computing the spread further comprises the steps of:
   calculating, for said specified particular window of time, a measure of central tendency of said threshold crossing intervals; and
   calculating, for said specified particular window of time, the variation of said threshold crossing intervals about said measure of central tendency.

4. A method for selecting from a plurality of different voltage threshold detectors that detector likely to yield the most reliable data to be utilized in determining whether the electrical activity of the heart is normal or abnormal, said method to be utilized with EKG monitoring devices, and said method comprising the steps of:
   specifying a particular window of time;
   identifying certain voltage threshold detectors as active during said specified window of time;
   recording the times at which a threshold of each of said active voltage threshold detectors was exceeded during said specified window of time;
   in response to said recorded times, assessing the temporal regularity of how often said threshold of each of said active voltage threshold detectors was exceeded;
   in response to said recorded times, calculating the time rate of occurrence at which each of said voltage thresholds for each of said active voltage threshold detectors was exceeded;
   in response to said assessed temporal regularity, forming a subset from the set made up of said active voltage threshold detectors, said subset consisting of said active voltage threshold detectors assessed as having high temporal regularity; and
   designating an active voltage threshold detector within said subset with the highest assessed temporal regularity as that active voltage threshold detector likely to yield the most reliable data to be utilized in determining whether the electrical activity of the heart is normal or abnormal, unless said calculated time rates of occurrence for other active voltage threshold detectors within said subset with lower-in-magnitude thresholds are a predetermined multiple greater than one of said calculated time rate of occurrence for said active voltage threshold detector within said subset with the highest assessed temporal regularity, in which case said other active voltage threshold detectors within said subset with lower-in-magnitude thresholds with time rates of occurrence a predetermined multiple greater than one of said calculated time rate of occurrence for said active voltage threshold detector within said subset with the highest assessed temporal regularity are designated as those active voltage threshold detectors likely to yield the most reliable data to be utilized in determining whether the electrical activity of the heart is normal or abnormal.

5. The method of claim 4 wherein said recorded times have associated threshold crossing intervals, and said step of assessing the temporal regularity of how often said voltage thresholds of each of said active voltage threshold detectors was met or exceeded further comprises the step of computing the spread of the threshold crossing interval distribution.

6. The method of claim 5, wherein said step of computing the spread further comprises the steps of:
   calculating, for said specified particular window of time, a measure of central tendency of said threshold crossing intervals; and
   calculating, for said specified particular window of time, the variation of said threshold crossing intervals about said measure of central tendency.

7. A method for selecting from a plurality of different voltage threshold detectors that detector likely to yield the most reliable data to be utilized in determining whether the electrical activity of the heart is normal or abnormal, said method to be utilized with EKG monitoring devices, and said method comprising the steps of:
   specifying a particular window of time;
   identifying certain voltage threshold detectors as active during said specified window of time;
   recording the times at which a threshold of each of said active voltage threshold detectors was exceeded during said specified window of time;
   in response to said recorded times, assessing the temporal regularity of how often said threshold of each of said active voltage threshold detectors was exceeded;
   in response to said recorded times, calculating the time rate of occurrence at which each of said voltage thresholds for each of said active voltage threshold detectors was exceeded;
   in response to said assessed temporal regularity, forming a subset from the set made up of said active voltage threshold detectors, said subset consisting of said active voltage threshold detectors assessed as having high temporal regularity;
   selecting from said subset certain of said active voltage threshold detectors, the first of said certain active voltage threshold detectors being that with the highest assessed temporal regularity, and the rest of said certain active voltage threshold detectors being those with assessed temporal regularity essentially the same as that of said first certain active threshold detector with the highest assessed temporal regularity; and
   designating at least one of said rest of said certain active voltage threshold detectors as those active voltage threshold detectors likely to yield the most reliable data to be utilized in determining whether the electrical activity of the heart is normal or abnormal if said calculated time rates of occurrence for said at least one of said rest of said certain active voltage threshold detectors are some multiple greater than one of said calculated time rate of occurrence for said first certain active voltage threshold detector with the highest assessed temporal regularity, but otherwise designating said first certain active detector with the highest assessed temporal regularity as that active voltage threshold detector likely to yield the most reliable data to be utilized in determining whether the electrical activity of the heart is normal or abnormal.

8. The method of claim 7, wherein said step of designating further comprises the steps of:
   comparing said calculated time rate of occurrence for said first selected voltage threshold detector with said calculated time rates of occurrence for said rest of said certain active voltage threshold detectors;

designating at least one of said rest of said certain active voltage threshold detectors as likely to yield the most reliable data to be utilized in determining whether the electrical activity of the heart is normal or abnormal if said calculated time rates of occurrence for said rest of said certain active voltage threshold detectors are greater than or equal to two times that of said first certain voltage threshold detector with the highest assessed temporal regularity; and designating said first certain active voltage threshold detector with the highest assessed temporal regularity as likely to yield the most reliable data to be utilized in determining whether the electrical activity of the heart is normal or abnormal if said calculated time rates of occurrence for said rest of said certain active voltage threshold detectors are less than two times that of said first certain active voltage threshold detector with the highest assessed temporal regularity.

9. The method of claim 7 wherein said recorded times have associated threshold crossing intervals, and said step of assessing the temporal regularity of how often said voltage thresholds of each of said active voltage threshold detectors was met or exceeded further comprises the step of computing the spread of the threshold crossing interval distribution.

10. The method of claim 9, wherein said step of computing the spread further comprises the steps of:
calculating, for said specified particular window of time, a measure of central tendency of said threshold crossing intervals; and
calculating, for said specified particular window of time, the variation of said threshold crossing intervals about said measure of central tendency.

11. A system for selecting from a plurality of different voltage threshold detectors that detector likely to yield the most reliable data to be utilized in determining whether the electrical activity of a heart is normal or abnormal, said system to be utilized with EKG monitoring devices, and said system comprising:
means for specifying a particular window of time;
means for identifying certain voltage threshold detectors as active during said specified window of time;
means for recording the times at which a threshold of each of said active voltage threshold detectors was exceeded during said specified window of time;
means for, in response to said recorded times, assessing the temporal regularity of how often said threshold of each of said active voltage threshold detectors was exceeded; and
means for, in response to said assessed temporal regularity, designating at least one of said active voltage threshold detectors as likely to yield the most reliable data to be utilized in determining whether the electrical activity of the heart is normal or abnormal.

12. The system of claim 11 wherein said recorded times have associated threshold crossing intervals, and said means for assessing the temporal regularity of how often said voltage thresholds of each of said active voltage threshold detectors was met or exceeded further comprises means for computing the spread of the threshold crossing interval distribution.

13. The system of claim 12, wherein said means for computing the spread further comprises:
means for calculating, for said specified particular window of time, a measure of central tendency of said threshold crossing intervals; and
means for calculating, for said specified particular window of time, the variation of said threshold crossing intervals about said measure of central tendency.

14. A system for selecting from a plurality of different voltage threshold detectors that detector likely to yield the most reliable data to be utilized in determining whether the electrical activity of the heart is normal or abnormal, said system to be utilized with EKG monitoring devices, and said system comprising:
means for specifying a particular window of time;
means for identifying certain voltage threshold detectors as active during said specified window of time;
means for recording the times at which a threshold of each of said active voltage threshold detectors was exceeded during said specified window of time;
means for, in response to said recorded times, assessing the temporal regularity of how often said threshold of each of said active voltage threshold detectors was exceeded;
means for, in response to said recorded times, calculating the time rate of occurrence at which each of said voltage thresholds for each of said active voltage threshold detectors was exceeded;
means for, in response to said assessed temporal regularity, forming a subset from the set made up of said active voltage threshold detectors, said subset consisting of said active voltage threshold detectors assessed as having high temporal regularity; and
means for designating an active voltage threshold detector within said subset with the highest assessed temporal regularity as that active voltage threshold detector likely to yield the most reliable data to be utilized in determining whether the electrical activity of the heart is normal or abnormal, unless said calculated time rates of occurrence for other active voltage threshold detectors within said subset with lower-in-magnitude thresholds are a predetermined multiple greater than one of said calculated time rate of occurrence for said active voltage threshold detector within said subset with the highest assessed temporal regularity, in which case said other active voltage threshold detectors within said subset with lower-in-magnitude thresholds with time rates of occurrence a predetermined multiple greater than one of said calculated time rate of occurrence for said active voltage threshold detector within said subset with the highest assessed temporal regularity are designated as those active voltage threshold detectors likely to yield the most reliable data to be utilized in determining whether the electrical activity of the heart is normal or abnormal.

15. The system of claim 14 wherein said recorded times have associated threshold crossing intervals, and said means for assessing the temporal regularity of how often said voltage thresholds of each of said active voltage threshold detectors was met or exceeded further comprises means for computing the spread of the threshold crossing interval distribution.

16. The system of claim 15, wherein said means for computing the spread further comprises:
means for calculating, for said specified particular window of time, a measure of central tendency of said threshold crossing intervals; and
means for calculating, for said specified particular window of time, the variation of said threshold crossing intervals about said measure of central tendency.

17. A system for selecting from a plurality of different voltage threshold detectors that detector likely to yield the most reliable data to be utilized in determining whether the electrical activity of the heart is normal or abnormal, said system to be utilized with EKG monitoring devices, and said system comprising the steps of:

means for specifying a particular window of time;

means for identifying certain voltage threshold detectors as active during said specified window of time;

means for recording the times at which a threshold of each of said active voltage threshold detectors was exceeded during said specified window of time;

means for, in response to said recorded times, assessing the temporal regularity of how often said threshold of each of said active voltage threshold detectors was exceeded;

means for, in response to said recorded times, calculating the time rate of occurrence at which each of said voltage thresholds for each of said active voltage threshold detectors was exceeded;

means for, in response to said assessed temporal regularity, forming a subset from the set made up of said active voltage threshold detectors, said subset consisting of said active voltage threshold detectors assessed as having high temporal regularity;

means for selecting from said subset certain of said active voltage threshold detectors, the first of said certain active voltage threshold detectors being that with the highest assessed temporal regularity, and the rest of said certain active voltage threshold detectors being those with assessed temporal regularity essentially the same as that of said first certain active threshold detector with the highest assessed temporal regularity; and means for designating at least one of said rest of said certain active voltage threshold detectors as those active voltage threshold detectors likely to yield the most reliable data to be utilized in determining whether the electrical activity of the heart is normal or abnormal if said calculated time rates of occurrence for said at least one of said rest of said certain active second selected voltage threshold detectors are some multiple greater than one of said calculated time rate of occurrence for said first certain active voltage threshold detector with the highest assessed temporal regularity, but otherwise designating said first certain active detector with the highest assessed temporal regularity as that active voltage threshold detector likely to yield the most reliable data to be utilized in determining whether the electrical activity of the heart is normal or abnormal.

18. The system of claim 17, wherein said means for designating further comprises:

means for comparing said calculated time rate of occurrence for said first selected voltage threshold detector with said calculated time rates of occurrence for said rest of said certain active voltage threshold detectors;

means for designating at least one of said rest of said certain active voltage threshold detectors as likely to yield the most reliable data to be utilized in determining whether the electrical activity of the heart is normal or abnormal if said calculated time rates of occurrence for said rest of said certain active voltage threshold detectors are greater than or equal to two times that of said first selected voltage threshold detector with the highest assessed temporal regularity; and means for designating said first certain active voltage threshold detector with the highest assessed temporal regularity as likely to yield the most reliable data to be utilized in determining whether the electrical activity of the heart is normal or abnormal if said calculated time rates of occurrence for said rest of said certain active voltage threshold detectors are less than two times that of said first certain active voltage threshold detector with the highest assessed temporal regularity.

19. The system of claim 17 wherein said recorded times have associated threshold crossing intervals, and said means for assessing the temporal regularity of how often said voltage thresholds of each of said active voltage threshold detectors was met or exceeded further comprises means for computing the spread of the threshold crossing interval distribution.

20. The system of claim 19, wherein said means for computing the spread further comprises:

means for calculating, for said specified particular window of time, a measure of central tendency of said threshold crossing intervals; and means for calculating, for said specified particular window of time, the variation of said threshold crossing intervals about said measure of central tendency.

* * * * *